United States Patent
Franks et al.

(10) Patent No.: US 10,957,425 B1
(45) Date of Patent: Mar. 23, 2021

(54) SYSTEMS FOR CREATING AND MODIFYING A FILE FOR AN ENTITY, AND SYSTEMS FOR LOCATING RECORDS IN THE FILE

(71) Applicant: Allscripts Software, LLC, Chicago, IL (US)

(72) Inventors: Jeffrey W. Franks, Grand Rapids, MI (US); Tyler John Downs, Litchfield, IL (US); Ryan Durham, Pawnee, IL (US); Brad Emery, Phoenixville, PA (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 1258 days.

(21) Appl. No.: 14/945,071

(22) Filed: Nov. 18, 2015

(51) Int. Cl.
  *G16H 10/60* (2018.01)
  *G06F 19/00* (2018.01)
  *G06F 16/21* (2019.01)

(52) U.S. Cl.
  CPC .......... *G16H 10/60* (2018.01); *G06F 16/211* (2019.01); *G06F 19/36* (2013.01)

(58) Field of Classification Search
  None
  See application file for complete search history.

(56) References Cited

U.S. PATENT DOCUMENTS

| | | |
|---|---|---|
| 8,239,218 B1 | 8/2012 | Madras et al. |
| 8,725,537 B2 | 5/2014 | Lorsch |
| 8,768,725 B2 | 7/2014 | Lorsch |
| 2002/0026332 A1 | 2/2002 | Snowden et al. |
| 2004/0172307 A1 | 9/2004 | Gruber |
| 2005/0075909 A1 | 4/2005 | Flagstad |
| 2005/0086074 A1 | 4/2005 | Punzak et al. |
| 2006/0106645 A1 | 5/2006 | Bergelson et al. |
| 2007/0027715 A1 | 2/2007 | Gropper et al. |
| 2008/0306872 A1 | 12/2008 | Felsher |
| 2013/0030838 A1 | 1/2013 | Myers et al. |
| 2013/0304510 A1* | 11/2013 | Chen ............. G06Q 10/06 705/3 |
| 2013/0332194 A1* | 12/2013 | D'Auria .......... G16H 10/60 705/3 |

* cited by examiner

*Primary Examiner* — Devin C Hein
(74) *Attorney, Agent, or Firm* — Medley, Behrens & Lewis, LLC

(57) ABSTRACT

Described herein are various technologies pertaining to generating and modifying a file for an entity, wherein the file includes a file record, and further wherein the file record includes binary data and a schema that is usable to hydrate a record based upon the binary data. The file is modified by appending file records to one another, where file records optionally correspond to different record creation systems. Described herein are also various technologies pertaining to locating a record in the file.

20 Claims, 8 Drawing Sheets

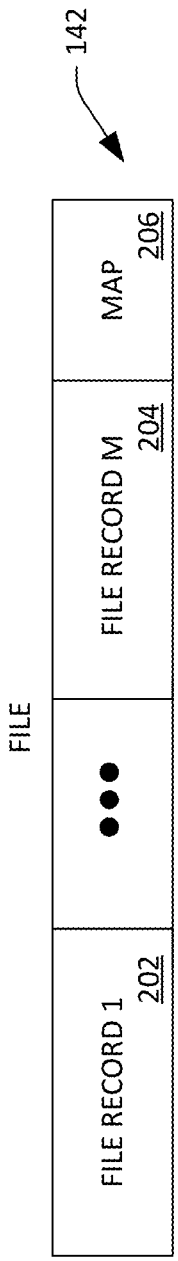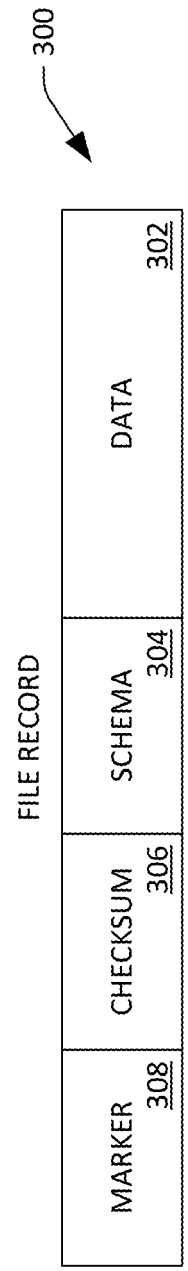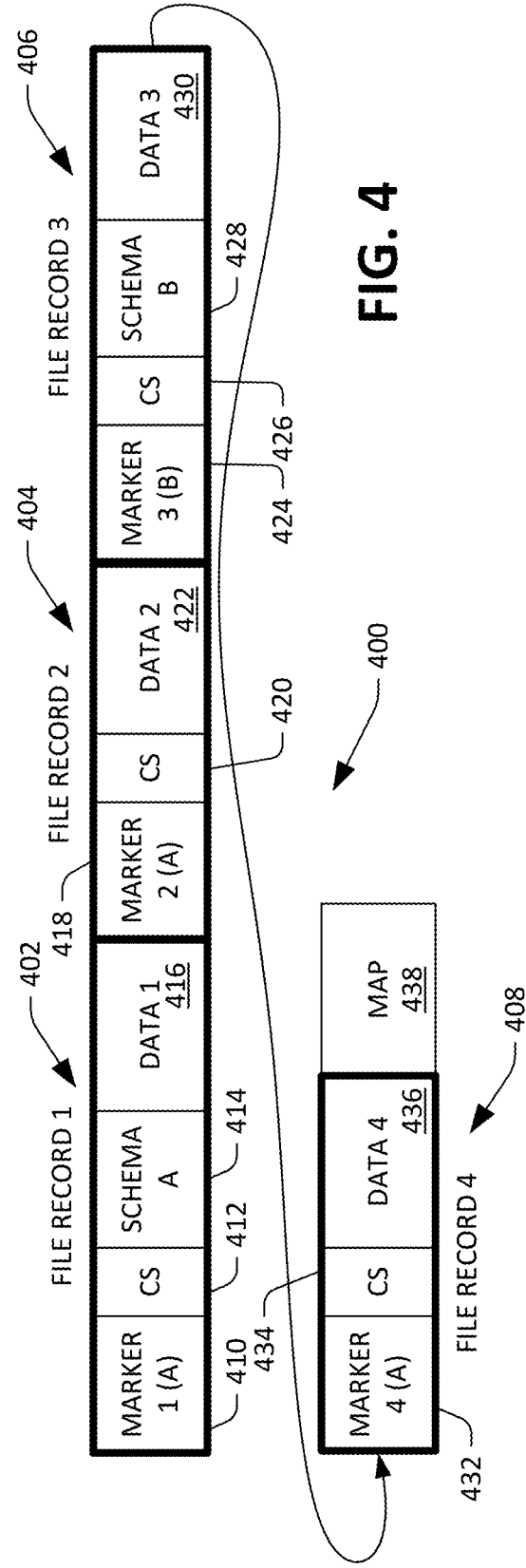

US 10,957,425 B1

SYSTEMS FOR CREATING AND MODIFYING A FILE FOR AN ENTITY, AND SYSTEMS FOR LOCATING RECORDS IN THE FILE

TECHNICAL FIELD

The aspects described herein are generally related to a computer system that is configured to create and/or modify a file for an entity, wherein the file includes file records that are based upon data generated by potentially different record creation systems.

BACKGROUND

Oftentimes, with respect to electronic record creation systems, records about an entity are formatted and stored in such a manner that the records are unable to be retrieved and deciphered unless a computing system has a record creation system utilized to create the records installed thereon. In a specific example, electronic health record (EHR) systems generate data about patients, and such data tends to be retained in silos. For instance, a patient may make an emergency room visit, and a hospital system that operates the emergency room may use a first EHR system to generate and store patient records. Sometime thereafter, the patient may visit an orthopedic surgery center, where the center utilizes a second EHR system to generate and store patient records. Conventionally, a healthcare worker at the orthopedic surgery center is unable to access the records about the patient generated and stored by the first EHR system. Instead, the healthcare worker must contact the hospital that operates the emergency room, whereupon the hospital will provide a summary of a patient record of interest to the healthcare worker at the orthopedic surgery center (presuming that the patient consented to the sharing of the patient record).

Further, using current technology, it may be difficult to acquire data about a patient from a patient record generated by a single EHR system. More specifically, aggregate results of EHR system databases that are developed over long periods of time often leads to bifurcation of data entries within a patient record (generated or stored via the EHR system) due to the gradual pace of change, feature alterations, bug fixes, loss of platform support, employee turnover at EHR system vendors, and so forth. Therefore, in an example, a patient record may be stratified across different records in the EHR system database of the hospital; hence, to retrieve data for a patient from the EHR system, multiple queries may need to be executed over multiple databases of the EHR system, which is computationally expensive and time consuming.

Moreover, when an end user is navigating to different parts of the patient record within a graphical user interface (GUI) of the EHR system, time consuming screen refreshes may be required, as only portions of the patient record are being pulled from one or more databases based upon a location of the end user in the GUI.

This paradigm of record generation and storage, where data is retained in individual silos, is relatively inefficient and may be detrimental to the patient. For example, during the aforementioned emergency room visit, a healthcare worker in the emergency room may have performed a blood test on the patient, wherein the blood test results (e.g., "normal" or "abnormal") are based upon the values of ten separate blood parameters. A surgeon at the orthopedic surgery center may be interested in a particular one of those parameters; for example, iron count in the blood of the patient. Conventionally, however, the EHR system at the hospital is configured to generate a summary rollup of the blood test results (which may be based upon multiple portions of the patient record retrieved from different databases of the EHR system at the hospital), where the summary rollup may indicate that the blood test results are "normal." The summary rollup, however, does not include the detail desired by the surgeon. Hence, the surgeon may order another blood test to be performed on the patient, which can be costly and generally undesired by the patient.

SUMMARY

The following is a brief summary of subject matter that is described in greater detail herein. This summary is not intended to be limiting as to the scope of the claims.

Described herein are various technologies pertaining to generating a file for an entity, wherein the file is created or modified in response to receiving data about the entity that has been generated by a record creation system. In a non-limiting example, the entity may be a patient, and the record creation system may be an electronic health record (EHR) system. A file is created when initial data about the entity is received at a computing device, where the data is generated by a first record creation system. Upon receipt of this data, the computing device creates a file record that makes up a portion of the file. The file record includes: 1) the data about the entity (e.g., in its raw, binary format); and 2) a schema that defines a mapping between the data about the entity and a format of a record about the entity, where the schema may be particular to the first record creation system. Thus, the schema can used by the first record creation system when storing a record about the entity in computer-readable storage.

Since the schema is stored in the file along with the aforementioned data about the entity, the record about the entity can be produced by a computing system regardless of whether or not the first record creation system is installed on the computing system. The computing device can also create the file record to include a marker that identifies the beginning of the file record and further identifies the schema that corresponds to the data in the file record. The computing device can further create the file record to include a checksum of the data about the entity. Additionally, the computing device can generate a map portion that is appended to an end of the file record, wherein the map portion includes a location of the file record in the file and a location of the schema in the file.

Subsequently, in an example, a second record creation system may generate second data about the entity, wherein the second data is to be included in the file. In response to receipt of the second data, the computing device can create a second file record and append the second file record to the file record described above. The second file record can include: 1) the second data about the entity (e.g., in its raw, binary format); and 2) a second schema that defines a mapping between the second data about the entity and a format of a second record about the entity, where the second schema may be particular to the second record creation system. Similar to what has been described above, the second record about the entity can be produced based upon the second data about the entity and the second schema in the second file record. Further, the second file record can additionally include a marker that identifies a beginning of the second file record and further identifies the second schema. The second file record can also include a checksum for the second data. The computing device can then update the map portion to include a location of the second file record in the file and a location of the second schema in file. The computing device then appends the map portion to the end of the second file record (e.g., the map portion is at the end of the file).

The computing device can add file records to the file as other data about the entity is received from one or more record creation systems (regardless of which record creation system generated the data). The computing device appends a new file record to an end of the most recent file record in the file; therefore, the file can be characterized as being continuous, as the file grows as more data about the entity is generated by record creation systems. It can be understood that the file may include any schema a single time—in other words, the schema corresponding to the first record creation system need not be stored in the file for each file record in the file that corresponds to the first record creation system. Further, the file can include an arbitrary number of file records, which include respective representations of records generated by an arbitrary number of different record creation systems.

The features described above are particularly well-suited for utilization in connection with patient records. A patient file having the format described above may, therefore, include representations of patient records over a relatively long period of time generated by numerous EHR systems. Patient files can be stored in a repository that is accessible by way of a suitable network. A healthcare worker can employ a client computing device to retrieve at least a portion of a patient file from the repository, for instance, based upon a unique patient identifier. The client computing device may then hydrate records about the patient using the schemas that are retained in the file. Thus, the client computing device used to retrieve the patient file can hydrate the patient records without having installed on the client computing device any EHR systems used to create the patient records. This allows a healthcare worker, for example, to quickly acquire raw data in a patient record without worrying about whether the healthcare worker has the EHR system (or an appropriate version of the EHR system) utilized to generate the record installed on the client computing device.

While the above summary relates to use of a file in the healthcare setting, it is to be understood that files having the format described above are also well-suited for other environments. For instance, a person may have her automobile serviced at a repair shop, and thereafter have body work performed at an auto-body shop. Using the technologies described herein, a searchable file can be created that allows the auto-body shop to quickly identify work performed on the automobile at the repair shop. Thus, files for any suitable type of entity can be created, updated, and searched over.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

FIG. 2 is a schematic of an exemplary file.

FIG. 3 is a schematic of an exemplary file record in the file.

FIG. 4 is a schematic of an exemplary file that comprises four file records.

DETAILED DESCRIPTION

Figure 1:
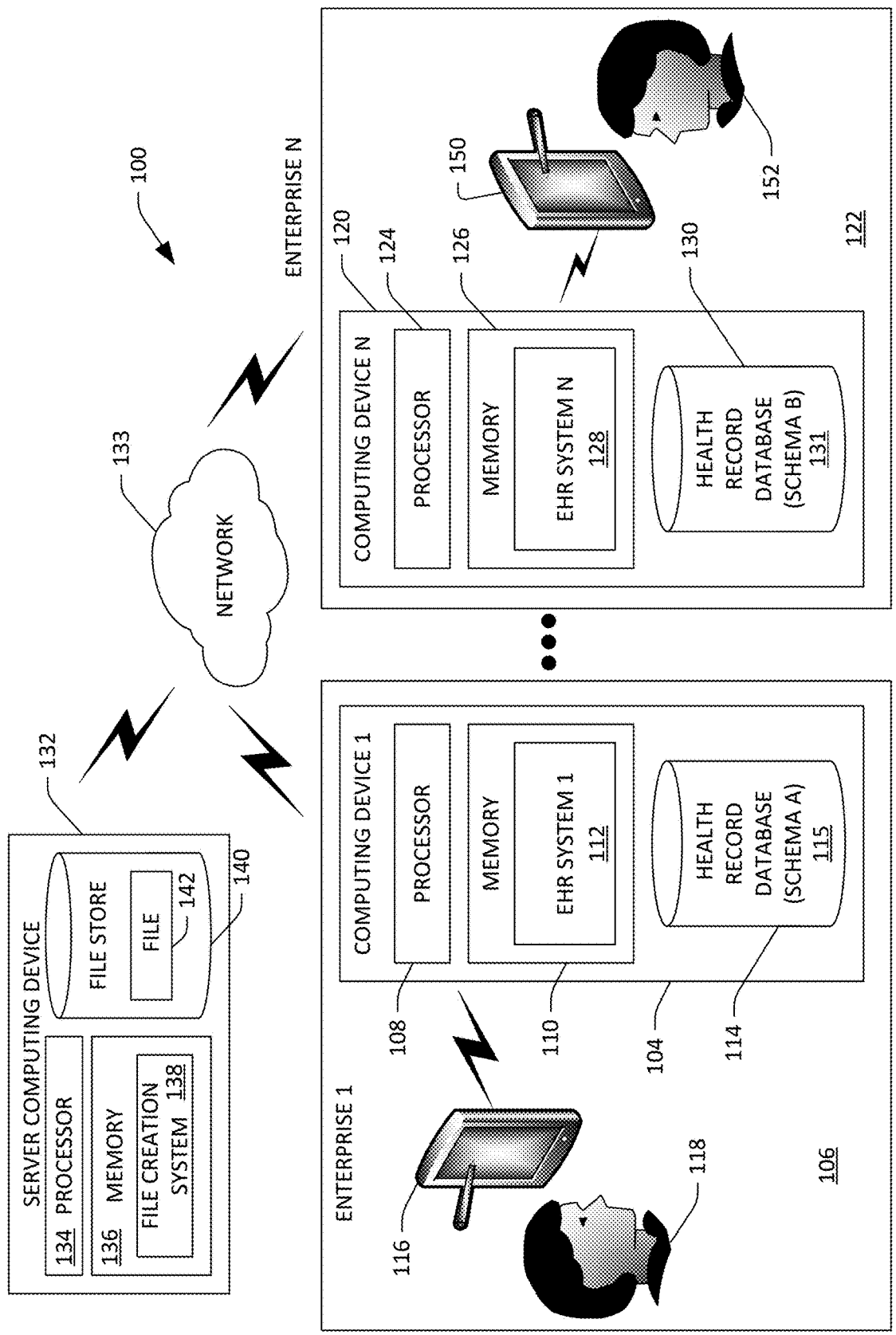
FIG. 1 is a functional block diagram of an exemplary system that facilitates generating a file, wherein at least one schema is stored in the file.

Various technologies pertaining to creating and modifying computer-readable files, as well as various technologies for locating records in such files, are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference. Moreover, the terms "first", "second", and so forth are used herein to distinguish between similarly-named entities, and are not intended to imply a sequence.

Various technologies pertaining to creating and modifying files are described herein. Various technologies pertaining to locating records in these files are also described herein. While the files are described herein as pertaining to patients, it is to be understood that the technologies described herein are applicable to generate and modify files pertaining to any suitable type of entity. For instance, the technologies described herein are applicable to create files for automobiles, computing equipment, or other suitable type of entity. Similarly, the technologies described herein are applicable to locate records in files for various types of entities.

With reference now to FIG. 1, an exemplary system 100 that facilitates generating and/or modifying a file for a patient is illustrated. The system 100 includes a first computing device 104 included in a first enterprise 106. In an example, the first enterprise 106 may be a healthcare facility, such as a hospital, an urgent care facility, a family doctor facility, etc. The computing device 104 includes a processor 108 and memory 110 that comprises instructions that are executed by the processor 108. As shown, the memory 110 includes a first electronic health record (EHR) system 112. Generally, the first EHR system 112 is configured to facilitate creation, storage, and maintenance of EHRs for patients of the first enterprise 106. The first computing device 104 further comprises a data repository 114 that includes a health record database 115. The health record database 115 comprises data about the patients of the first enterprise 106, wherein the data is typically stored in the data repository 114 in binary format and in accordance with a schema (schema A).

The system 100 may further include a first client computing device 116 that is employed by a healthcare worker 118 to generate EHRs about patients and/or retrieve data about patients from the health record database 115 in the data repository 114. For example, the first client computing device 116 may have a program or programs installed thereon that interface with the EHR system 112 to: 1) create EHRs for retention in the health record database 115; and/or 2) retrieve EHRs from the health record database 115. For instance, the healthcare worker 118 can utilize the first client computing device 116 to set forth notes pertaining to an electrocardiogram reading, and the notes and the reading can be transmitted to the first computing device 104, where the first EHR system 112 stores such information in the health record database 115 in conformance with schema A.

The system 100 can further include an nth computing device 120 of an nth enterprise 122. The nth enterprise 122 can be, for example, a hospital, a family physician's office, an urgent care center, etc. The nth computing device 120 includes a processor 124 and memory 126, wherein the memory 126 includes instructions that are executed by the processor 124. The memory 126, as shown, comprises an nth EHR system 128, wherein the nth EHR system 128 is configured to create, maintain, and store health records about patients of the nth enterprise 122. The nth EHR system may be an entirely different EHR system when compared to the first EHR system 112 installed on the first computing device 104. In another example, the first EHR system 112 and the nth EHR system may different versions of the same EHR system.

The nth computing device 120 further includes a data repository 130 that comprises a health record database 131, wherein the health record database 131 comprises data about patients stored in accordance with an nth schema (schema B). Therefore, the nth EHR system 128 stores the data about the patients of the nth enterprise 122 in the health record database 131 in accordance with schema B, which is different from schema A.

The system 100 may further include a second client computing device 150 that is employed by a second healthcare worker 152 at the nth enterprise 122 to generate EHRs about patients and/or retrieve data about patients from the health record database 131. For example, the second client computing device 150 may have a program or programs installed thereon that interface with the nth EHR system 128 to: 1) create EHRs for retention in the health record database 131; and/or 2) retrieve EHRs from the health record database 131. For instance, the healthcare worker 152 can utilize the second client computing device 150 to enter thermometer readings taken over a range of time, and the thermometer readings can be transmitted to the nth computing device 120, where the nth EHR system 128 stores such information in the health record database 131 in conformance with schema B. While the client computing devices 116 and 150 have been described above as being within the respective enterprises 106 and 122, in other examples computing devices external to the enterprises 106 and 122 can present data to the EHR systems 112 and 128. For example, a patient of the first enterprise 106 can update her patient record by way of the first EHR system 112 through use of a personal computing device of the patient (e.g., by providing user credentials to a web service when the patient is at home). Likewise, a patient of the nth enterprise 122 can update her patient record by way of the nth EHR system 128 through use of a personal computing device of the patient. It is therefore to be understood that patient records can be created or updated via computing devices that are external to the enterprises 106 and 122.

The system 100 can further include a server computing device 132 that is in communication with the first computing device 104 and the nth computing device 120 by way of a suitable network 133 (e.g. the Internet). The server computing device 132 comprises a processor 134 and memory 136, wherein the memory 136 includes instructions that are executed by the processor 134. In the system 100, the memory 136 includes a file creation system 138 that is configured to generate and/or modify patient files for patients of the first enterprise 106 and/or patients of the nth enterprise 122. The server computing device 132 also comprises a file store 140 that comprises a file 142 for a patient. While the file store 140 is illustrated as including a single file, it is to be understood that the file store 140 can include files for many patients of the first enterprise 106 and/or the nth enterprise 122.

Operation of the file creation system 138 is now set forth. The server computing device 132 can receive data about a patient from the first computing device 104, wherein the data about the patient has been generated or captured by the first EHR system 112 and is stored in the health record database 115 in conformance with schema A. Thus, the data about the patient received from the first computing device 104 is representative of patient encounter data generated or captured by way of the first EHR system 112. In a non-limiting example, the server computing device 132 can issue a pull command to the first computing device 104 to retrieve the data about the patient from the first computing device 104. In another example, the first computing device 104 can be configured to push the data about the patient to the server computing device 132. This push can occur periodically or immediately responsive to the data about the patient being produced by the EHR system 112 (e.g., in response to receiving data from the first client computing device 116).

When the file store 140 in of the server computing device 132 does not include a file for the patient, the file creation system 138 can create the file 142 for the patient in response to receipt of the data about the patient from the first computing device 104. To create the file 142, the file creation system 138 creates a file record for inclusion in the file 142. The file record is generally representative of the above-referenced patient encounter data generated or captured by the first EHR system 112. The file record created by the file creation system 138 includes the data about the patient received from the first computing device 104 (e.g., in its raw binary form as retained in the health record database 115). The file record also includes schema A—the schema used by the first EHR system 112 when storing the EHR in the health record database 115. Pursuant to an example, schema A may be provided to the server computing device 132 by the first EHR system 112 (e.g., a company that developed the first EHR system 112 may expose schema A). In another example, schema A can be learned over time, wherein schema A is learned based upon computer analysis of operation of the first EHR system 112. In still yet another example, schema A can be manually created based upon knowledge of operation of the first EHR system 112 by a subject matter expert. Still further, schema A can be estimated based on conformance to a list of known or common schema "rules" that are predefined, where conformance of the data to such rules allows a computing system to recognize or create schema A.

The file record created by the file creation system 138 can further include a marker that identifies the beginning of the file record. The marker can further include an identifier for schema A, thereby indicating that the data in the file record can be used to hydrate a health record for the patient using schema A. The term "hydrate", as used herein, is intended to encompass acts of defining a structure of a health record using a schema (e.g., schema A), and subsequently populating the health record with data in the file record through use of the schema. Moreover, the file record can include a checksum for the data in the file record and/or a combination of the data and schema A.

The file creation system 138, responsive to creating the file record, can append a map portion to the file record, such that the file 142 includes the file record and the map portion. The map portion can comprise an identifier for the file record and a location of the file record in the file 142. More specifically, in an example, the map portion can comprise a location of the marker in the file record. Further, the map portion can include a timestamp corresponding to the file record, which is indicative of a time when the EHR represented by the file record was created. Moreover, the map portion can include a location of schema A in the file 142.

The file creation system 138 can then serialize the file record and the map portion to form the file 142. The file creation system 138 may also optionally compress and encrypt the file 142. As will be described in greater detail below, the file may be provided to a computing device that requests the file 142 for the patient. The requesting computing device can hydrate a record for the patient using the data in the file record of the file 142 and schema A in the file record of the file 142. The requesting computing device can hydrate the record for the patient regardless of whether the computing device has the first EHR system 112 installed thereon. This is possible since the schema (schema A) is included in the file 142. Further, this patient record can be hydrated regardless of whether the first EHR system 112 is ever updated to use a different schema to generate and/or store data, as schema A remains static in the file 142.

The file creation system 138 can modify the file 142 by including additional file records in the file 142 and then updating the map portion. More particularly, when new data is received by the file creation system 138, the file creation system 138 can generate a new file record and append the new file record to a most recent file record in the file 142. The file creation system 138 can then update the map portion and append the map portion to the end of the newly created file record. Updating of the file 142 is explained by way of an example. Subsequent to the patient visiting the first enterprise 106, the patient may visit the nth enterprise 122, where the nth EHR system 128 creates new patient encounter data for the patient and formats the new patient encounter data for storage in the health record database 131 in conformance with schema B. The server computing device 132 can receive this formatted data about the patient from the nth computing device 120. The file creation system 138, in response to receiving this data from the nth computing device 120, retrieves the file 142 from the file store 140, decompresses and decrypts the file 142 if necessary, deserializes the file 142, and identifies an end of the most recently added file record in the file 142.

The file creation system 138 can generate a new file record that includes: 1) the data received from the nth computing device 120; and 2) schema B (as well as a marker and checksum, as described above). The file creation system 138 then appends the new file record to the end of the last file record in the file 142, and updates the map portion so that it includes an identifier for the new file record, a location of the new file record in the file 142, a timestamp for the new file record, and a location of schema B in the file 142. The file creation system 138 then appends the map portion to the end of the new record, serializes the file 142, optionally compresses and encrypts the file 142, and returns the file 142 to the file store 140. It can therefore be ascertained that, in this example, the file 142 includes raw data generated by at least two different EHR systems (the first EHR system 112 and the nth EHR system 128), and the file 142 further includes respective schemas (schema A and schema B) that can be utilized by a requesting computing device to hydrate records for the patient based upon content of the file 142, regardless of whether the requesting computing device has either the first EHR system 112 or the nth EHR system 128 installed thereon.

Now referring to FIG. 2, an exemplary schematic of the file 142 is depicted. The file 142 comprises a plurality of file records 202-204 that are appended to one another. The file records 202-204 are arranged in the file 142 based upon times when patent encounter data, respectively corresponding to the file records 202-204, were generated or captured by respective EHR systems. Thus, more specifically, the first file record 202 corresponds to first patient encounter data, while the mth file record 204 corresponds to mth patient encounter data that was created or captured subsequent to the first patient encounter data. Therefore, the file records 202-204 are arranged in the file 142 from oldest (at the beginning of the file 142) to newest (at the end of the file 142). The file 142 also includes a map portion 206 that is appended to the mth (last) file record 204 in the file 142. As described previously, the map portion 206 identifies locations of the file records 202-204 in the file 142, as well as locations of schemas in the file 142.

Now referring to FIG. 3, a schematic of an exemplary file record 300 that can be included in the file 142 is illustrated. The file record 300 comprises binary (raw) data 302 received from the data storage associated with an EHR system. The file record 300 additionally comprises a schema 304 that can be used to hydrate a record with the data 302. The file record 300 also comprises a checksum 306 for the file record 300, where the checksum is over the data 302 and/or a combination of the data 302 and the schema 304. Generally, the checksum 306 is used when the file is read to ensure lack of corruption. The checksum 306 can further be used to skip file records when the file 142 is read by a computer processor. The file record 300 also comprises a marker 308, wherein the marker 308 indicates a beginning of the file record 300. Further, the marker 308 can include an identifier for the schema 304. The file record 300 is arranged in the manner shown in FIG. 3., with the marker 308 being at the beginning of the file record 300, the checksum 306 being immediately after the marker 308, the schema 304 being immediately after the checksum 306, and the binary payload (data 302) being immediately after the schema 304. Other arrangements, however, are contemplated.

Now referring to FIG. 4, an exemplary file 400 is illustrated. The exemplary file 400 comprises four file records 402, 404, 406, and 408. The first file record 402 comprises a first marker 410, a first checksum 412, schema A 414, and first data 416. The second file record 404 includes a second marker 418, a second checksum 420, and second data 422. It is to be noted that the second marker 418 indicates that the second data 422 corresponds to schema A 414, which is included in the first file record 402. Schema A 414, however, is not included in the second file record 404. It is, therefore, to be understood that schema A 414 need only be retained in the file 400 a single time, even though multiple file records may include data that corresponds to schema A 414.

The third file record 406 includes a third marker 424, a third checksum 426, schema B 428, and third data 430. As can be ascertained, the third marker 424 indicates that the third data 430 corresponds to schema B 428. Further, the third file record 406 includes schema B 428, as schema B 428 has not been previously included in any preceding file records in the file 400. The fourth file record 408 includes a fourth marker 432, a fourth checksum 434, and fourth data 436. The fourth marker 432 indicates that the fourth data 436, in the fourth file record 408, corresponds to schema A 414. Again, however, schema A 414 is not included in the fourth file record 408, as it has been previously included in the first file record 402 in the file 400. The file 400 also includes a map portion 438, which will be described in greater detail below.

Figure 5:
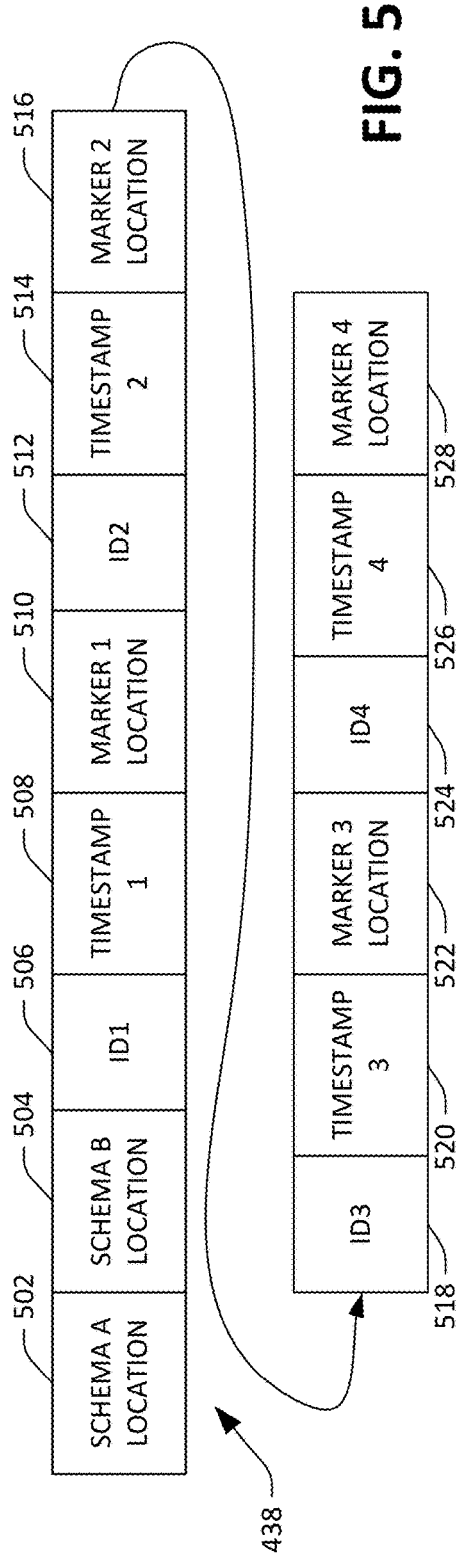
FIG. 5 is a schematic of a map portion of the file shown in FIG. 4.

Turning now to FIG. 5, a schematic of the map portion 438 of the file 400 is illustrated. The map portion 438 includes a location 502 of schema A 414 in the file 400. The map portion 438 also includes a location 504 of schema B 428 in the file 400. These locations 502 and 504 can be used when the file 400 is read to identify the locations of schema A 414 and schema B 428 in the file 400 when hydrating records using such schemas (particularly when the schemas are not included in a file record of interest). The map portion 438 also includes an identifier 506 of the first file record 402, a timestamp 508 corresponding to the first file record 402, and a location 510 of the marker 410 of the first file record 402 in the file 400.

The map portion 438 also includes an identifier 512 for the second file record 404, a timestamp 514 for the second file record 404, and a location 516 of the marker 418 of the second file record 404 in the file 400. Similarly, the map portion 438 includes an identifier 518 of the third file record 406, a timestamp 526 of the third file record 406, and a location 522 of the marker 424 of the third file record 406 in the file 400. Finally, the map portion 438 includes an identifier 524 of the fourth file record 408, a timestamp 526 of the fourth file record 408, and a location 528 of the marker 432 of the fourth file record 408 in the file 400.

The map portion 438 is accessed initially when the file 400 is read. Specifically, a clinician may wish to retrieve patient encounter data represented by the second file record 404 in the file 400. To retrieve such patient encounter data, the clinician can employ a client computing device to retrieve the file 400 and can set forth a query, where the query identifies the second file record 404 in the file 400. In response to receipt of the query, the client computing device can seek to the end of the file 400 and analyze the map 438. Using the map portion 438, the client computing device can identify the identifier 512 of the second file record 404, and can further ascertain the location 516 of the marker 418 for the second file record 404. The client computing device may then seek to the marker location 516 in the file 400, where schema A is identified in the marker 418. The client computing device may then find the location 502 of schema A in the map portion 438, and can retrieve schema A from the first file record 402. The client computing device can then hydrate the record using the second data 422 and schema A 414.

The map portion 438 is also useful when records are located in the file 400 based upon temporal attributes. For example, a physician may only wish to review records that were generated within the last 60 days. The client computing device can seek to the map portion 438, and can analyze the timestamps 508, 514, 520, and 526 such that only file records corresponding to the queried time period are used to hydrate records. The map portion 438 is further well-suited for custody management. For instance, the patient may cease using the services of a physician, and may wish that the physician not have access to health data in the file 400 that occurred after the physician was let go by the patient.

Figure 6:
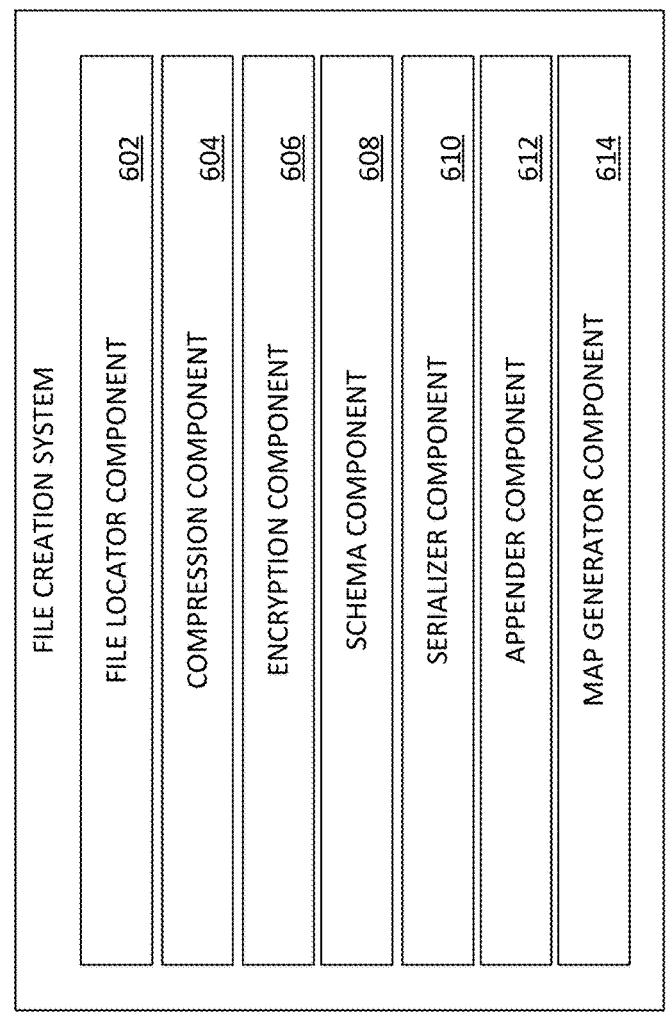
FIG. 6 is a functional block diagram of an exemplary file creation system.

Now referring to FIG. 6, a functional block diagram of the file creation system 138 is illustrated. The file creation system 138 includes a file locator component 602 that is configured to search the file store 140 for a file for a patient in response to receiving data about the patient from one of the computing devices 104 or 120. When the file locator component 602 determines that a file already exists for the patient in the file store 140, the file locator component 602 retrieves the file from the file store so that the file can be modified to include a new file record. When the file locator component 602 is unable to locate a file for the patient in the file store 140, the file creation system 138 can begin the process of creating a new file for the patient.

The file creation system 138 optionally also includes a compression component 604 that is configured to compress and/or decompress files. For example, files in the file store 140 may be compressed. Therefore, when the file locator component 602 identifies that a file exists for the patient in the file store 140, the compression component 604 can decompress the file, such that a new file record is able to be appended to the file. The file creation system 138 may also include an encryption component 606 that is configured to encrypt and/or decrypt files. Files in the file store 140 may be encrypted; hence, when the file locator component 602 determines that a file exists for the patient, the encryption component 606 can decrypt the file, such that a new record can be appended to the file.

The file creation system 138 also includes a schema component 608 that is configured to retrieve a schema that corresponds to the data received from the computing device 104 or the computing device 120. For instance, the schema component 608 may have access to a data store of schemas for various different EHR systems, and can select the appropriate schema based upon an identity of the EHR system utilized to create the data received by the file creation system 138. The file creation system 138 can also include a serializer component 610 that is configured to serialize and/or deserialize data. For example, files in the file store may be serialized for storage purposes. When the file locator component 602 determines that a file exists for the patient (and subsequent to the file being decompressed and/or decrypted), the serializer component 610 can deserialize the file. An appender component 612 may then create a file record that includes: 1) the data received from the computing device 104 or the computing device 120; and 2) the schema retrieved by the schema component 608. The appender component 612 can then append the file record to the last file record in the file (if it exists). The file creation system 138 also includes a map generator component 614 that generates or updates a map portion for the file and appends the map portion to the last file record in the file. The serializer component 610 may then serialize the file, the encryption component 606 can encrypt the file, and the compression component 604 can compress the file (the order of these actions may alter). The file creation system 138 can then cause the file to be stored in the file store 140.

Figure 7:
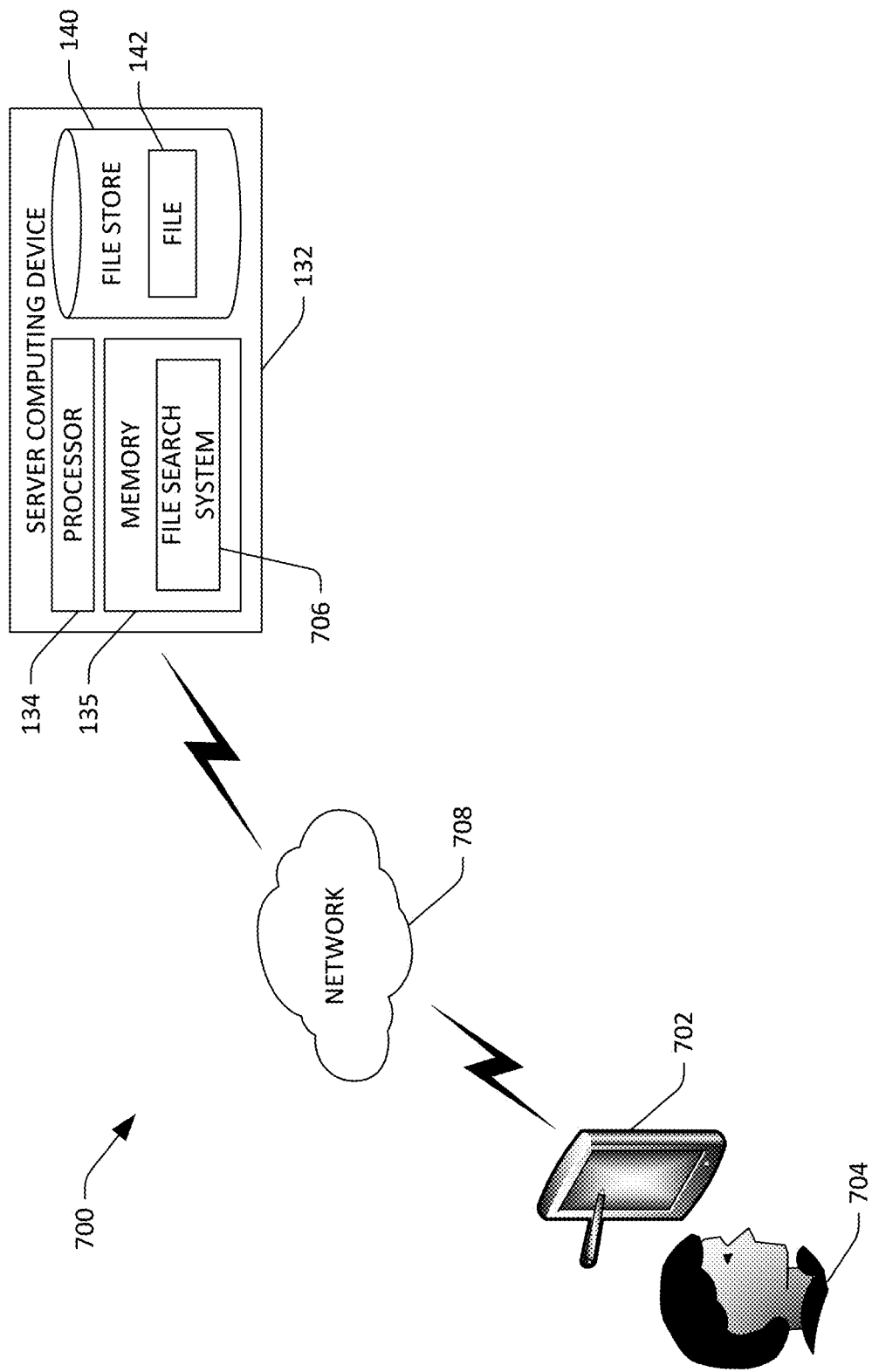
FIG. 7 is a functional block diagram of an exemplary system that facilitates transmission of a file to a computing device in response to receipt of a query.

Now referring to FIG. 7, an exemplary system 700 that facilitates provision of the file to a requesting client computing device is illustrated. The system 700 includes a client computing device 702 employed by a healthcare worker 704, where the client computing device 702 is in communication with the server computing device 132 by way of a network 708 (e.g., the Internet). The healthcare worker 704 employs the client computing device 702 to generate a request for the file 142 and transmit the request to the server computing device 132. The memory 136 of the server computing device 132 includes a file search system 706 that can access the file store 140. The file search system 706, in response to receiving the request for the file 142 from the client computing device 702, transmits the file 142 to the client computing device 702 by way of the network 708. The client computing device 702, therefore, has the file 142 stored thereon, and the client computing device 702 can extract data from the file 142.

Figure 8:
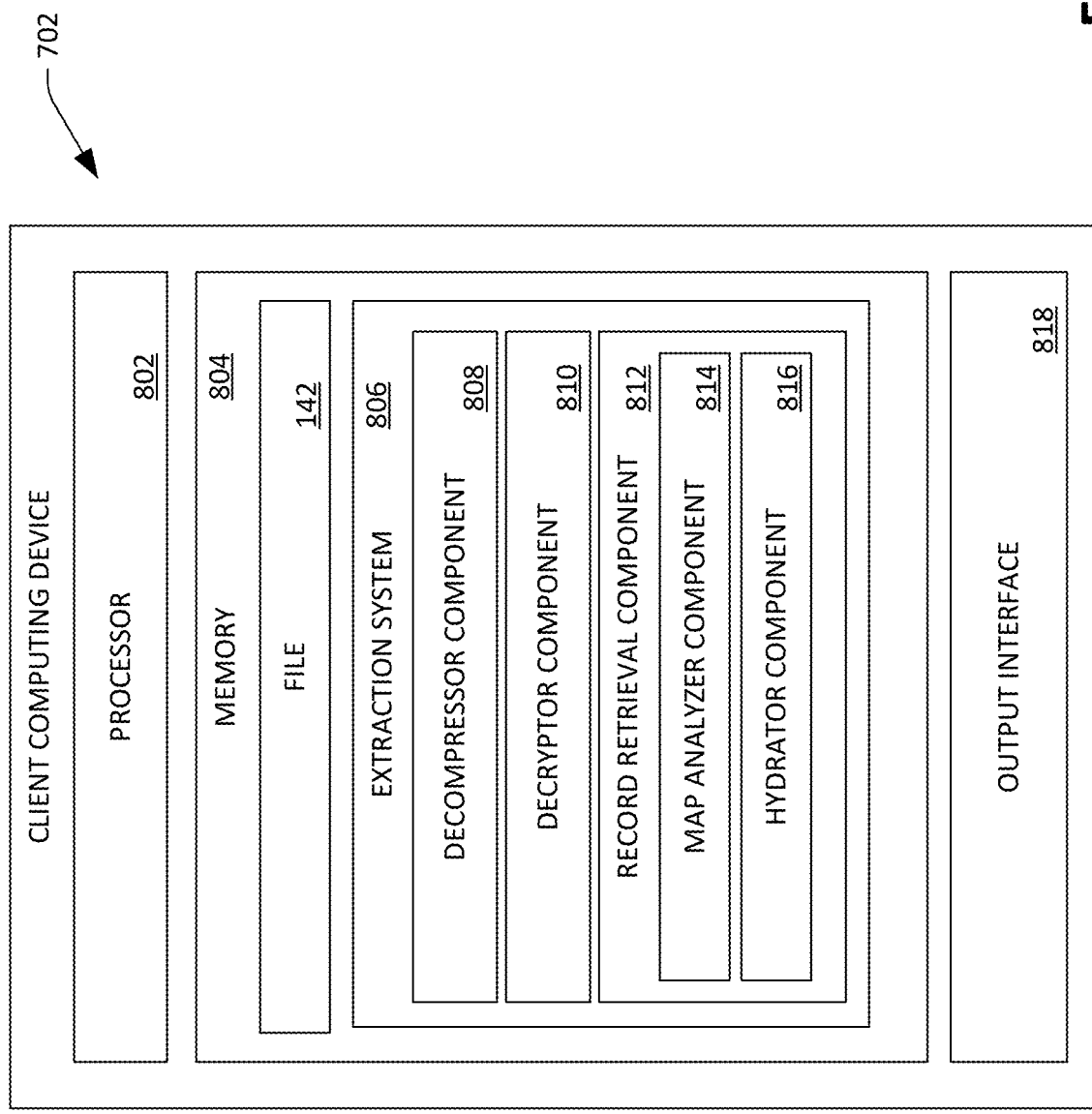
FIG. 8 is a functional block diagram of a client computing device that is configured to locate a record in a file.

Now referring to FIG. 8, a functional block diagram of the client computing device 702 is illustrated. The client computing device 702 includes a processor 802 and memory 804. The memory 804 comprises the file 142 retrieved from the file store 140 of the server computing device 132. The memory 804 also includes an extraction system 806 that is executed by the processor 802. The extraction system 806 comprises a decompressor component 808 that can decompress the file 142 (if compressed). The extraction system 806 can also include a decryptor component 810 that can decrypt the file 142 (if encrypted).

The extraction system 806 also includes a record retrieval component 812 that is configured to extract information from the file 142. For example, the record retrieval component 812 can receive a query submitted by the healthcare worker 704 via the client computing device 702, wherein the query can include data that identifies file records in the file 142. For instance, as referenced above, the query can include an identifier for a file record in the file 142, parameters pertaining to file records the file 142 (such as time), etc.

The record retrieval component 812 comprises a map analyzer component 814. The map analyzer component 814 seeks to the end of the file 142 to analyze the map portion of the file 142 based upon the query. The record retrieval component 812 can identify one or more records in the file 142 based upon the analysis performed by the map analyzer component 814 (e.g., records identified by the map component that pertain to the query). The record retrieval component 812 may also include a hydrator component 816 that can hydrate an electronic record based upon: 1) data in a file record identified by the record retrieval component 812; and 2) a corresponding schema included in the file 142. Once such record has been hydrated, various functions can be performed. For example, a "diff" operation can be performed to identify differences between certain electronic records. In another example, the record retrieval component 812 can be configured to automatically retrieve the most recent file record in the file 142 and hydrate a record based upon its contents. This may be beneficial, as oftentimes a healthcare worker wishes to see the most recent record in a patient file. The client computing device 702 also includes an output interface 818, such as a display, a speaker, or the like. Information pertaining to at least one hydrated record can be presented to the healthcare worker 704 by way of the output interface 818.

It can be ascertained that the technologies described above are advantageous over the conventional data storage paradigm, as information about an entity can be acquired more efficiently through utilization of, for example, the file 142. For example, if a clinician wished to retrieve patient encounter data from a patient record utilizing conventional approaches, numerous databases (with data potentially structured in accordance with numerous schemas) may be queried (and potentially re-queried) to locate the desired data, the data may then need to be translated, and finally loaded for presentation. In contrast, using the file 142 for the patient, the patient encounter data can be quickly located by searching through a single file, where the map is searched, the appropriate schema is pulled, and the requested data is loaded.

Figure 9:
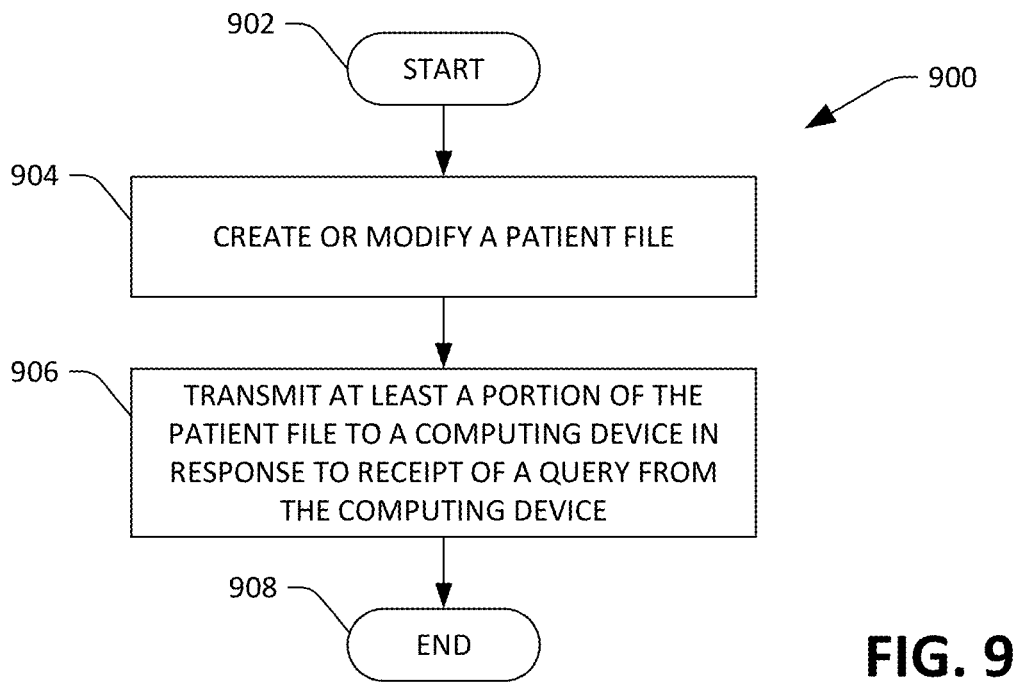
FIG. 9 is a flow diagram illustrating an exemplary methodology for creating or modifying a patient file and transmitting at least a portion of the file to a computing device.
Figure 11:
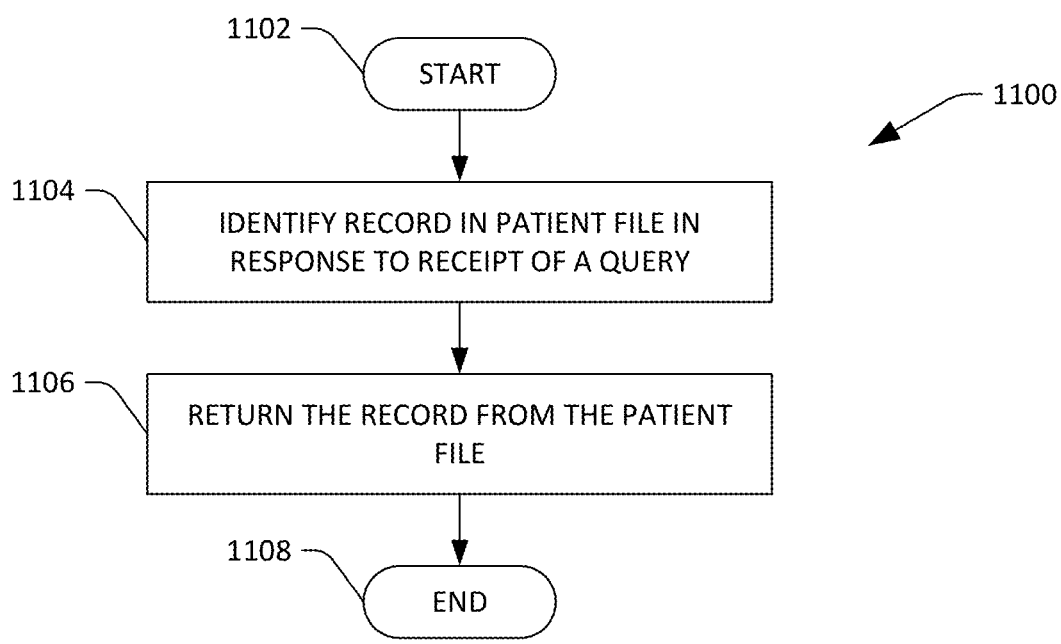
FIG. 11 is a flow diagram illustrating an exemplary methodology for locating a record in a patient file.
Figure 10:
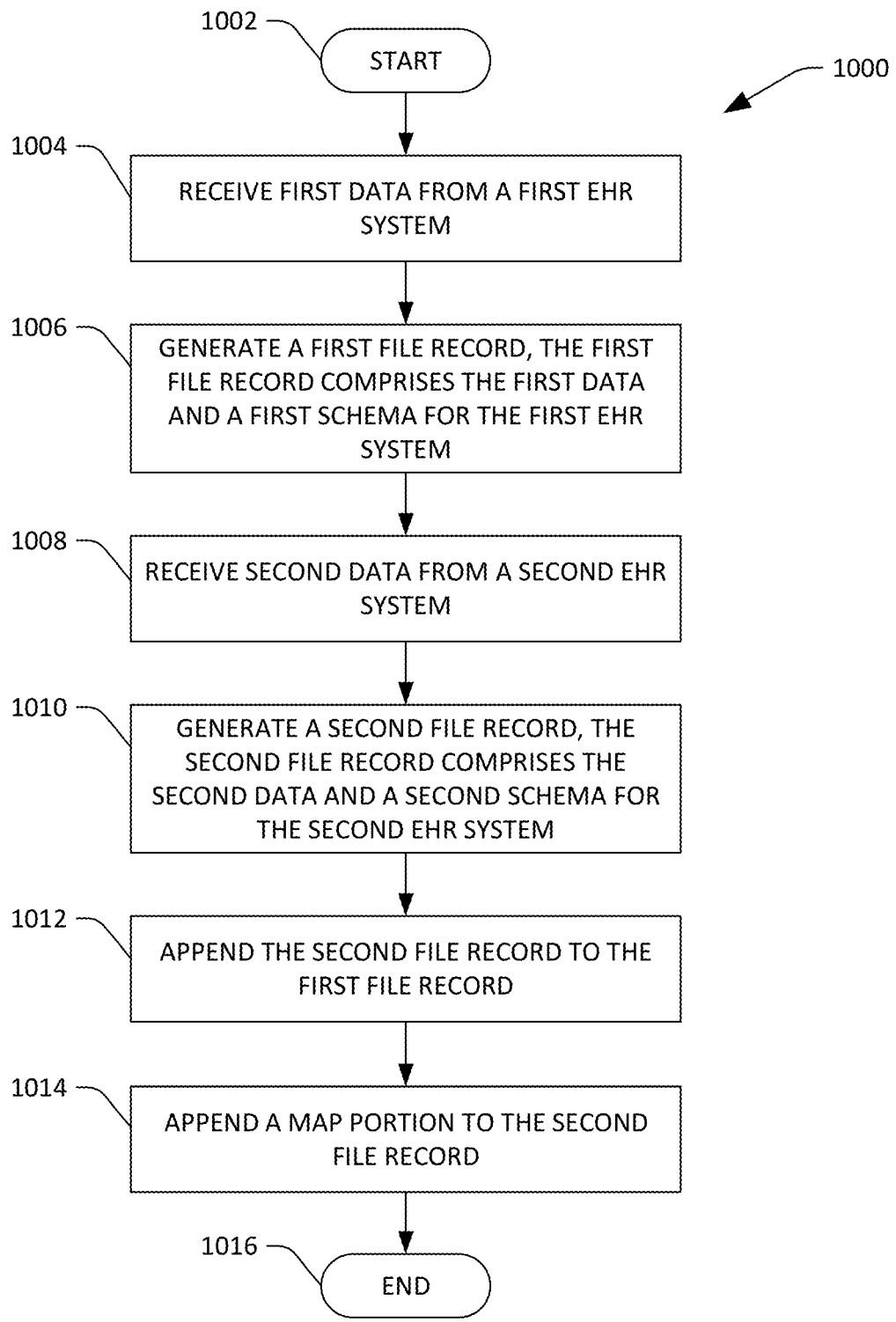
FIG. 10 is a flow diagram that illustrates an exemplary methodology for creating and modifying a patient file.

FIGS. 9-11 illustrate exemplary methodologies relating to creating and modifying files, as well as locating records in such files. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Turning now solely to FIG. 9, an exemplary methodology 900 that facilitates creating and/or modifying a patient file is illustrated. The methodology 900 starts at 902, and at 904, a patient file is created or modified, wherein creation or modification of the patient file is performed in response to receiving data about the patient, wherein the data is generated by an EHR system. As described above, creating or modifying the patient file includes storing, in a computer readable storage device and as at least a portion of the file: 1) the received data about the patient; and 2) a schema, wherein the schema describes a data format used by the EHR system when creating and/or storing the data about the patient.

At 906, at least a portion of the patient file is transmitted to a computing device in response to receipt of a query from the computing device. The computing device that receives the patient file can hydrate (or otherwise consume the contents of) a patient record with the data about the patient by using the schema and/or map included in the file record. The methodology 900 completes at 908.

Now referring to FIG. 10, an exemplary methodology 1000 that facilitates creating and modifying a patient file is illustrated. The methodology 1000 starts at 1002, and at 1004, first data about a patient from a first EHR system is received. At 1006, a first file record is generated, where the first file record comprises the first data about the patient and a first schema used by the first EHR system when generating and/or storing the first data.

Later, at 1008, second data about the patient from a second EHR system is received. At 1010, a second file record is generated, where the second file record comprises the second data about the patient and a second schema used by the second EHR system to generate and/or store the second data. At 1012, the second file record is appended to the first file record, and at 1014 a map portion is appended to the end of the second file record. The methodology 1000 completes at 1016.

With reference now to FIG. 11, an exemplary methodology 1100 that facilitates locating a record in a patient file is illustrated. The methodology 1100 starts 1102, and at 1104 a record in the patient file is located in response to receipt of a query. As described previously, the query can identify at least one file record in the patient file and/or a parameter corresponding to the at least one file record in the patient file. The record can be identified based upon analysis of the map portion of the patient file. At 1106, the record is returned. The methodology 1100 completes at 1108.

Figure 12:
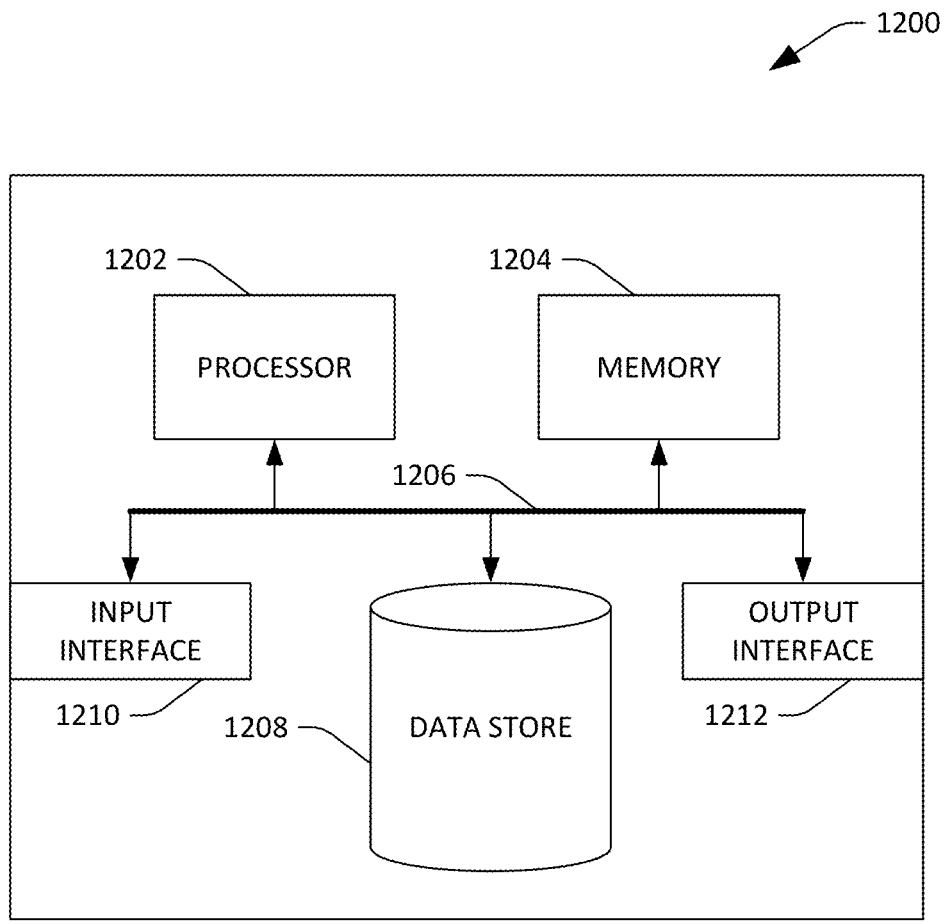
FIG. 12 is an exemplary computing device.

Referring now to FIG. 12, a high-level illustration of an exemplary computing device 1200 that can be used in accordance with the systems and methodologies disclosed herein is illustrated. For instance, the computing device 1200 may be used in a system that is configured to create and/or modify a file. By way of another example, the computing device 1200 can be used in a system that is configured to search over contents of a file. The computing device 1200 includes at least one processor 1202 that executes instructions that are stored in a memory 1204. The instructions may be, for instance, instructions for implementing functionality described as being carried out by one or more components discussed above or instructions for implementing one or more of the methods described above. The processor 1202 may access the memory 1204 by way of a system bus 1206. In addition to storing executable instructions, the memory 1204 may also store data about patients, including files, file records, etc.

The computing device 1200 additionally includes a data store 1208 that is accessible by the processor 1202 by way of the system bus 1206. The data store 1208 may include executable instructions, patient files, etc. The computing device 1200 also includes an input interface 1210 that allows external devices to communicate with the computing device 1200. For instance, the input interface 1210 may be used to receive instructions from an external computer device, from a user, etc. The computing device 1200 also includes an output interface 1212 that interfaces the computing device 1200 with one or more external devices. For example, the computing device 1200 may display text, images, etc. by way of the output interface 1212.

It is contemplated that the external devices that communicate with the computing device 1200 via the input interface 1210 and the output interface 1212 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 1200 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 1200 may be a distributed system. Thus, for instance, several devices may be in communication by way of a network connection and may collectively perform tasks described as being performed by the computing device 1200.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A method performed by a processor of a server computing device, comprising:
receiving, from a first computing device that utilizes a first electronic health record (EHR) system, data about a patient, wherein the data about the patient has been generated by a first record creation system of the first EHR system, wherein the first record creation system generates the data about the patient according to a first schema, the first schema defines a first mapping between the data about the patient and a format of a health record of the first EHR system;
in response to receiving the data about the patient from the first computing device, creating or modifying a file for the patient, wherein creating or modifying the file comprises:
storing, in a computer-readable storage device and as at least a portion of the file:
the data about the patient; and
the first schema;
receiving, from a second computing device that utilizes a second EHR system, a query that corresponds to the data about the patient, wherein the second EHR system utilizes a second record creation system that is configured to generate and produce data of the second EHR system according to a second schema, the second schema defines a second mapping between the data of the second EHR system and a format of health records of the second EHR system; and
in response to receiving the query, transmitting the at least the portion of the file to the second computing device, wherein the second computing device produces the data about the patient by:
locating the data about the patient and the first schema in the at least the portion of the file;
defining a structure of the health record of the first EHR system using the first schema in the at least the portion of the file; and
populating the structure of the health record with the data about the patient in the at least the portion of the file according to the first schema in the at least the portion of the file.

2. The method of claim 1, further comprising:
in response to receiving second data about the patient from the second EHR system, modifying the file for the patient, wherein modifying the file comprises:
storing, in the computer-readable storage device as a second portion of the file:
the second data about the patient; and
the second schema.

3. The method of claim 2, further comprising:
storing the data about the patient and the first schema as a portion of a first record of the file; and
storing the second data about the patient and the second schema as a portion of a second record of the file.

4. The method of claim 3, wherein the first record of the file further comprises:
a first marker that identifies the first schema that corresponds to the data about the patient in the first record; and
wherein the second record of the file further comprises:
a second marker that identifies the second schema that corresponds to the second data about the patient in the second record.

5. The method of claim 4, wherein creating or modifying the file further comprises:
appending a map portion to the second record, the map portion comprises:
a pointer to the first schema;
a pointer to the second schema;
data that identifies a location of the first marker in the file; and
data that identifies a location of the second marker in the file.

6. The method of claim 3, wherein modifying the file further comprises:
appending the second record of the file to the first record of the file; and
appending a map portion of the file to the second record of the file, the map portion of the file comprises data that identifies a location of the first record in the file and data that identifies a location of the second record in the file.

7. The method of claim 1, further comprising:
responsive to receiving the data about the patient, serializing the data about the patient prior to storing the data about the patient as at least the portion of the file.

8. The method of claim 1, wherein creating or modifying the file further comprises:
storing a map portion as a part of the file, the map portion comprises a timestamp that is indicative of when the first EHR system created the data about the patient.

9. The method of claim 1, further comprising:
responsive to creating or modifying the file and prior to transmitting the at least the portion of the file, at least one of encrypting or compressing the file.

10. A computing system comprising:
a processor; and
memory that stores instructions that, when executed by the processor, cause the processor to perform acts comprising:
receiving, from a first computing device that utilizes a first record creation system, data about an entity, wherein the data about the entity has been generated by the first record creation system, wherein the first record creation system generates the data about the entity according to a first schema, the first schema defines a first mapping between the data about the entity and a format of a record of the first record creation system;
creating or modifying a file for the entity in response to receiving the data about the entity generated by the first record creation system of the entity, wherein creating or modifying the file comprises:
generating a file record, the file record comprises:
the data about the entity; and
the first schema; and
storing the file record as a portion of the file in a computer-readable data repository;
receiving, from a second computing device that utilizes a second record creation system, a query that is indicative of the data about the entity, the second computing device is in network communication with the computing system, wherein the second record creation system is configured to generate and produce data of the second record creation system according to a second schema, the second schema defines a second mapping between the data of the second record creation system and a format of records of the second record creation system; and in response to receiving the query, transmitting at least the file record to the second computing device, wherein the second computing device produces the file record about the entity by:
locating the data about the entity and the first schema in the at least the file record;
defining a structure of the record of the first record creation system using the first schema in the at least the file record; and
populating the structure of the record with the data about the entity in the at least the file record according to the first schema in the at least the file record.

11. The computing system of claim 10, wherein the entity is a patient and the first record creation system is a first electronic health record (EHR) system.

12. The computing system of claim 10, the acts further comprising:
modifying the file in response to receiving second data about the entity generated by the first record creation system, wherein modifying the file comprises:
generating a second file record, the second file record comprises the second data about the entity, wherein the second file record fails to include the first schema; and
appending the second file record to the file, wherein the first computing device produces a second record about the entity based upon the second data about the entity and the first schema in the file record.

13. The computing system of claim 12, wherein modifying the file in response to receiving the second data further comprises:
generating a map portion, the map portion comprises data that identifies a location of the first schema in the file record; and
appending the map portion to the second file record.

14. The computing system of claim 13, the map portion further comprises:
an identifier of the file record;
a location of the file record in the file;
an identifier of the second file record; and
a location of the second file record in the file.

15. The computing system of claim 14, the map portion further comprises:
a first timestamp for the file record; and
a second timestamp for the second file record.

16. The computing system of claim 10, the acts further comprising:
modifying the file in response to receiving second data about the entity generated by the second record creation system, wherein modifying the file comprises:
generating a second file record, the second file record comprises:
the second data about the entity; and
the second schema; and
appending the second file record to the file record in the file; and
transmitting at least the second file record to the first computing device in response to receiving a second query from the first computing device, wherein the first computing device produces the second record about the entity based upon the second data about the entity and the second schema.

17. The computing system of claim 16, the acts further comprising:
modifying the file in response to receiving third data about the entity generated by the first record creation system, wherein modifying the file comprises:
generating a third file record, the third file record comprises the third data about the entity, the third file record fails to comprise the first schema; and
appending the third file record to the second file record in the file; and
transmitting at least the third file record to the computing device in response to receiving the query from the computing device, wherein the computing device produces a third record about the entity based upon the third data about the entity and the first schema in the file record.

18. The computing system of claim 17, wherein modifying the file in response to receiving the third data further comprises appending a map portion to the third file record in the file, the map portion comprises data that identifies locations of the file record, the second file record, and the third file record in the file.

19. The computing system of claim 10, the file record further comprises a marker, the marker identifies the first schema that is usable by the second computing device to produce the file record.

20. A computer-readable storage medium comprising instructions that, when executed by a processor, cause the processor to perform acts comprising:
creating a file in computer-readable storage for a patient, the file comprises:
a first record, the first record comprises:
first data about the patient, the first data about the patient based upon a first electronic health record for the patient generated by a first record creation system of a first electronic health record (EHR) system; and
a first schema that defines a first mapping between the first data about the patient and a format of the first electronic health record of the first EHR system, wherein the first record creation system has generated the first record according to the first schema;
a second record, the second record comprises:
second data about the patient, the second data about the patient based upon a second electronic health record for the patient generated by a second record creation system of a second electronic health record (EHR) system; and
a second schema that defines a second mapping between the second data about the patient and a format of the second electronic health record of the second EHR system, wherein the second record creation system has generated the second record according to the second schema; and
a map portion that identifies a location of the first record in the file and a location of the second record in the file;
receiving, from a computing device and over a network connection, a query that corresponds to the first data and the second data, wherein the computing device fails to have at least one of the first record creation system of the first EHR system or the second record creation system of the second EHR system installed thereon; and in response to receiving the query, transmitting, to the computing device and over the network connection, the file, wherein the computing device produces the first data about the patient by:

locating the first data about the patient and the first schema in the file based upon the map portion;

defining a structure of the first record using the first schema in the file; and populating the structure of the first record with the first data about the patient in the file according to the first schema in the file, and further wherein the computing device produces the second data about the patient by:

locating the second data about the patient and the second schema in the file based upon the map portion;

defining a structure of the second record using the second schema in the file; and populating the structure of the second record with the second data about the patient in the file according to the second schema in the file.

\* \* \* \* \*